United States Patent
Morken et al.

(10) Patent No.: US 7,071,346 B2
(45) Date of Patent: Jul. 4, 2006

(54) POLYMERS, CONTAINING A FLUOROCYCLOBUTYL RING AND THEIR PREPARATION

(75) Inventors: Peter Arnold Morken, Wilmington, DE (US); Paul R. Resnick, Cary, NC (US); Lin Wang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 459 days.

(21) Appl. No.: 10/427,542

(22) Filed: May 1, 2003

(65) Prior Publication Data

US 2004/0014920 A1     Jan. 22, 2004

Related U.S. Application Data

(62) Division of application No. 09/807,253, filed as application No. PCT/US99/23194 on Oct. 5, 1999, now Pat. No. 6,620,899.

(60) Provisional application No. 60/104,340, filed on Oct. 15, 1998.

(51) Int. Cl.
*C07C 301/00*    (2006.01)

(52) U.S. Cl. .................. 558/59; 526/240; 526/243; 558/61

(58) Field of Classification Search .............. 558/59, 558/61; 526/240, 243
See application file for complete search history.

(56) References Cited

U.S. PATENT DOCUMENTS

| 2,462,347 A | 2/1949 | Barrick |
| 3,282,875 A | 11/1966 | Connolly et al. |
| 3,481,914 A | 12/1969 | Holler et al. |

FOREIGN PATENT DOCUMENTS

| WO | WO 94/03503 | 2/1994 |
| WO | WO 98/20573 | 5/1998 |

*Primary Examiner*—Bernard Lipman

(57) ABSTRACT

This invention concerns olefins having a terminally disposed fluorocyclobutyl ring bearing an ionic functionality or a precursor thereto, a process for the production thereof, and polymers formed therefrom.

10 Claims, 1 Drawing Sheet

POLYMERS, CONTAINING A FLUOROCYCLOBUTYL RING AND THEIR PREPARATION

This is a division of Ser. No. 09/807,253, filed Apr. 9, 2001, now U.S. Pat. No. 6,620,899, first filed as provisional application 60/104,340, on Oct. 15, 1998 and filed as International Application No. PCT/US/99/23194, on Oct. 5, 1999 and nationally in the United States on Apr. 9, 2001.

FIELD OF THE INVENTION

This invention pertains to olefins having a terminally disposed fluorocyclobutyl ring bearing an ionic functionality or a precursor thereto, a process for the production thereof, and polymers, especially ionomers, formed therefrom. The invention further pertains to ionically conductive compositions formed by the combination of a liquid and the ionomer of the invention, and electrochemical devices such as electrodes, sensors, and solid polymer electrolytes comprising those conductive compositions. The polymers of the invention are useful in the formation of films and coatings with high chemical resistance and good physical properties. The ionomers of the invention are useful in electrochemical applications, particularly in lithium batteries. The polymeric compositions of the invention are useful for strong acid catalysis, such as Friedel-Crafts alkylation.

BACKGROUND OF THE INVENTION

Barrick (U.S. Pat. No. 2,462,347) discloses the 2+2 cycloaddition of fluorinated ethylene whereof at least two of the hydrogens have been replaced by halogens of which at least two must be fluorines, to dienes having two terminally unsaturated bonds of which at least one must be ethylenic to form a fluorocyclo-butyl-containing terminal vinyl monomer. Conjugated dienes are preferred. Polymerization, or copolymerization with other unsaturated polymerizable compounds, is carried out in a free radical initiated process.

Glazkov et al., (Izvest. Akad. Nauk SSSR, Ser. Khim. 10, 2372ff, October 1988) disclose the 2+2 cycloaddition of fluorovinyl ethers to conjugated dienes, particularly 1,3-butadiene and 1,3-pentadiene the reaction occurring at the terminal, rather than the internal, double bond of the pentadiene. Reactants included fluorovinyl ethers of the general formula $R_fOCF=CF_2$, wherein $R_f$ is $CF_2CF(CF_3)O(CF_2)_2$ $SO_2F$. Synthesis of the cycloadduct was carried out at 120–140° C. for 6 hours in an autoclave. At temperatures above 150° C. and pressures of 5–10 kbar, the cyclic dimers of the fluorvinyl ethers were formed. Glazkov is silent regarding polymerization.

Roberts et al., (Organic Reactions, Vol. 12, Chapt 1, A. C. Cope, Ed. in Chief, John Wiley & Sons, Inc. New York, 1962) disclose conjugated dienes as highly reactive among unsaturated compounds in cycloaddition reactions with fluoroalkenes; unconjugated dienes are not mentioned. Similarly, Hudlicky (Chemistry of Organic Fluorine Compounds, 2nd ed. P. 450ff, Ellis Horwood PTR Prentice Hall, N.Y., 1992) dislcose 2+2 cycloaddition reactions between dienes and fluorinated ethylene, but only for conjugated dienes. Hudlicky also discloses the onset of cyclodimerization of reactants at temperature above 200° C.

Holler et al., (U.S. Pat. No. 3,481,914) discloses the polymerization of halogen-bearing olefins having a double bond in terminal position and having one of certain halogen-containing groups separated by at least two carbon atoms from said terminal vinyl group, the halogens being attached to primary, secondary, or aromatic carbons, but not to tertiary, allylic or benzylic carbons. Encompassed in the disclosure are terminal olefins having cyclobutyl rings with fluorine-containing substituents on the secondary carbons thereof. Polymerization is carried out by use of Ziegler-type coordination catalysts. Among the catalysts suitable are $TiCl_3$ in combination with Aluminum alkyl.

Coordination polymerization of olefins using metallocene catalysts is disclosed in Welborn et al., U.S. Pat. No. 5,324,800.

Brookhart et al., (WO 9623010A2) discloses a copolymer formed from ethene and a compound represented by the formula $H_2C=CH (CH_2)_aR_fR$, particularly 1,1,2,2-tetrafluoro-2-[(1,1,2,2,3,3,4,4-octafluoro-9-decenyl)oxy] ethanesulfonyl fluoride, via a catalyzed reaction employing diimine-transition metal complexes. The polymer so-formed comprises a polyethylene backbone having randomly distributed pendant groups of 1,1,2,2-tetrafluoro-2-[(1,1,2,2,3, 3,4,4-octafluoro-(mostly)octoxy] ethanesulfonyl fluoride, as well as alkyl branches. Brookhart's teachings are limited to comonomers having only secondary carbon atoms linking the fluorine-containing group and the olefinic double bond.

It has long been known in the art to form ionically conducting membranes and gels from organic polymers containing ionic pendant groups. Such polymers are known as ionomers. Particularly well-known ionomer membranes in widespread commercial use are Nafion® Membranes available from E. I. du Pont de Nemours and Company. Nafion® is formed by copolymerizing tetra-fluoro ethylene (TFE) with perfluoro(3,6-dioxa-4-methyl-7-octenesulfonyl fluoride), as disclosed in U.S. Pat. No. 3,282,875. Also known are copolymers of TFE with perfluoro (3-oxa-4-pentene sulfonyl fluoride), as disclosed in U.S. Pat. No. 4,358,545. The copolymers so formed are converted to the ionomeric form by hydrolysis, typically by exposure to an appropriate aqueous base, as disclosed in U.S. Pat. No. 3,282,875. Lithium, sodium and potassium are all well known in the art as suitable cations for the above cited ionomers.

Doyle et al., (WO 98/20573) disclose a highly fluorinated lithium ion exchange polymer electrolyte membrane (FLIEPEM) exhibiting a conductivity of at least 0.1 mS/cm comprising a highly fluorinated lithium ion exchange polymer membrane (FLIEPM), the polymer having pendant fluoroalkoxy lithium sulfonate groups, and wherein the polymer is either completely or partially cation exchanged; and, at least one aprotic solvent imbibed in said membrane. Electrodes and lithium cells are also disclosed.

In the polymers above-cited, the fluorine atoms provide more than one benefit. The fluorine groups on the carbons proximate to the sulfonyl group in the pendant side chain provide the electronegativity to render the cation sufficiently labile so as to provide high ionic conductivity. Replacement of those fluorine atoms with hydrogen results in a considerable reduction in ionic mobility and consequent loss of conductivity.

The remainder of the fluorine atoms, such as those in the polymer backbone, afford the chemical and thermal stability to the polymer normally associated with fluorinated polymers. This has proven to be of considerable value in such applications as the well-known "chlor-alkali" process. However, highly fluorinated polymers also have disadvantages where there is less need for high chemical and thermal stability. The fluorinated monomers are more expensive than their olefin counterparts, require higher processing temperatures, and often require expensive corrosion resistant processing equipment. Furthermore, it is difficult to form solutions and dispersions of fluoropolymers. Additionally, it is difficult to form strong adhesive bonds with fluoropolymers. In materials employed in electrochemical cells, for example, it may be advantageous to have better processibility at some cost to chemical and thermal stability. Thus, there is an incentive to develop ionomers with highly labile cations having reduced fluorine content.

Numerous publications disclose polyethers with either proximal ionic species in the polymer or in combination with ionic salts. Conductivities are in the range of $10^{-5}$ S/cm and less. Le Nest et al., Polymer Communications 28, 303 (1987) disclose a composition of polyether glycol oligomers joined by phosphate or thiophosphate moieties hydrolyzed to the related lithium ionomer. In combination with propylene carbonate, conductivity in the range of $1$–$10 \times 10^{-4}$ S/cm was realized. A review of the related art is found in Fauteux et al., Electrochimica Acta 40, 2185 (1995).

Benrabah et al., Electrochimica Acta, 40, 2259 (1995) disclose polyethers crosslinked by lithium oxytetrafluorosulfonates and derivatives. No aprotic solvents are incorporated. With the addition of lithium salts conductivity of $<10^{-4}$ S/cm was achieved.

Armand et al., U.S. Pat. No, 5,627,292 disclose copolymers formed from vinyl fluoroethoxy sulfonyl fluorides or cyclic ethers having fluoroethoxy sulfonyl fluoride groups with polyethylene oxide, acrylonitrile, pyridine and other monomers. Lithium sulfonate ionomers are formed. No aprotic solvents are incorporated. Conductivity was $<10^{-4}$ S/cm.

Narang et al., U.S. Pat. No. 5,633,098 disclose polyacrylate copolymers having a functionalized polyolefin backbone and pendant groups containing tetrafluoroethoxy lithium sulfonate groups. The comonomers containing the sulfonate groups are present in molar ratios of 50–100%. Compositions are disclosed comprising the polymer and a solvent mixture consisting of propylene carbonate, ethylene carbonate, and dimethoxyethane ethyl ether. Ionic conductivity of those compositions was in the range of $10^{-4}$–$10^{-3}$ S/cm.

SUMMARY OF THE INVENTION

The present invention provides for a substantially non-fluorinated polyolefin polymer comprising pendant groups comprising the radical of the formula

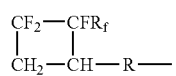
(I)

wherein R is oxygen or an alkylene or alkylene ether group wherein one or more of the hydrogens may be substituted by halogen, and $R_f$ is a radical of the formula

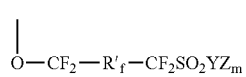
(II)

wherein $R_f'$ is a bond or is a fluoroalkylene or fluoroalkylene ether group, Y is F or O, Z is hydrogen or a univalent metal and m=0 or 1 with the proviso that m=0 when Y is F, and m=1 when Y is O, $R_f$ being ionizable, in character, when m=1.

The present invention further provides for a terminally unsaturated olefin of the formula

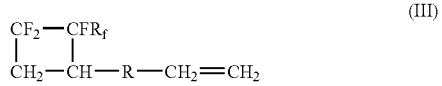
(III)

wherein R is oxygen or an alkylene or alkylene ether group wherein one or more of the hydrogens may be substituted by halogen, and $R_f$ is a radical of the formula

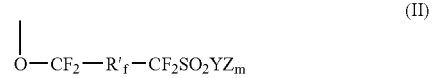
(II)

wherein $R_f'$ is a bond or is a fluoroalkylene or fluoroalkylene ether group, Y is F or O, Z is a univalent metal and m=0 or 1 with the proviso that m=0 when Y is F, and m=1 when Y is O, $R_f$ being ionizable in character when m=1.

Further provided is a process for producing a terminally unsaturated olefin, the process comprising combining in a vessel a diene of the formula

(IV)

wherein R is oxygen or an alkylene or alkylene ether group wherein one or more of the hydrogens may be substituted by halogen with up to 50 mol-% of a terminally unsaturated fluoroolefin having the formula

(V)

wherein $R_f'$ is a bond or is a fluoroalkylene or fluoroalkylene ether group, Y is F or O, Z is a univalent metal and m=0 or 1 with the proviso that m=0 when Y is F, and m=1 when Y is O. $R_f$ being ionizable in character when m=1;

heating to a temperature in the range of 180–600° C. for a period of about one second to about 24 hours. The process is preferably followed by cooling and removal of product.

Further provided is a polymerization process the process comprising the copolymerization of an olefin with the terminally unsaturated olefin (III), in the presence of an organometallic coordination catalyst, under polymerization conditions.

Further provided is an ionically conductive composition comprising the polymer having pendant groups (I) wherein, in (II), m=1 and Z is an alkali metal, and a liquid imbibed therewithin.

Further provided is a conductive composition comprising a liquid and the compound described by the formula (III) wherein, in (II), m=1 and Z is an alkali metal.

Further provided is an electrochemical cell comprising a cathode, an anode and a separator, at least one of which comprises the polymer having pendant groups (I) wherein, in (II), m=1 and Z is an alkali metal.

Further provided is an electrochemical cell comprising an anode, a cathode, a separator, and a conductive composition comprising the compound described by the formula (III) wherein, in (II), m=1 and Z is an alkali metal, and a liquid.

Further provided is an electrode comprising an electroactive material and the polymer having pendent groups (I) wherein, in (II), m=1 and Z is an alkali metal.

DETAILED DESCRIPTION

Figure 2:
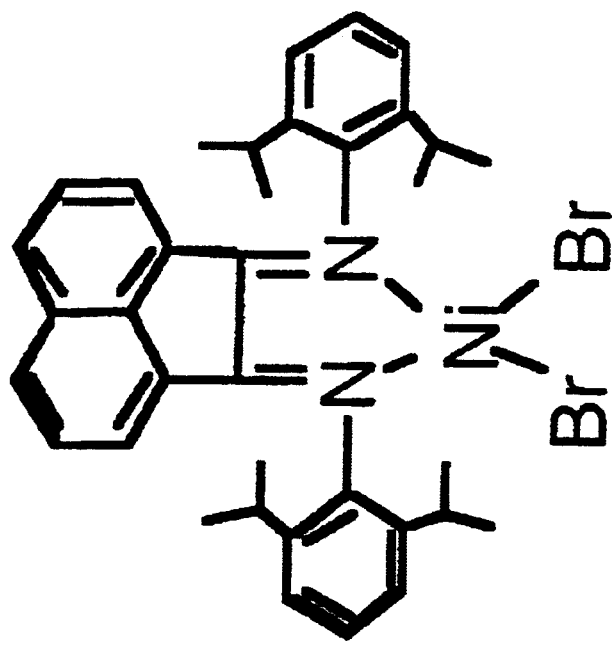
FIG. 2 depicts a nickel diimine catalyst.

The present invention is directed to a novel monomer, the method for its synthesis, and the polymer produced therefrom. The monomer of the invention is described by the formula

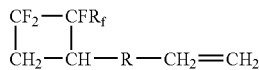 (III)

wherein R is an oxygen, alkylene or alkylene ether radical. Preferably R is an alkylene radical comprising from 2 to about 10 carbon atoms, preferably 2 to 6 carbon atoms, optionally substituted by one or more ether oxygens, and one or more of the hydrogens may be substituted by halogen. Most preferably, R is an ethenyl or butenyl radical. $R_f$ is a radical of the formula

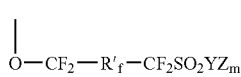 (II)

wherein $R_f'$ is a bond or is a fluoroalkylene or fluoroalkylene ether group, Y is F or O, Z is a univalent metal and m=0 or 1 with the proviso that m=0 when Y is F, and m=1 when Y is O, $R_f$ being ionizable in character when m=1.

In a preferred embodiment, $R_f$ is the radical represented by the formula

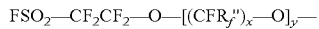

where $R_f''$ is perfluoroalkyl or fluorine, x=0, 1, 2, 3, or 4, y=0, 1, 2, or 3, with the proviso that when x=0, y=0. Most preferably, $R_f''$ is fluorine or trifluoromethyl, x=2, y=0 or 1. When x>1, the $R_f''$ groups need not be the same.

In a second preferred embodiment, $R_f$ is the radical represented by the formula

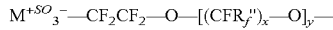

where $R_f''$ is perfluoroalkyl or fluorine, x=0, 1, 2, 3, or 4, y=0, 1, 2, or 3, with the proviso that when x=0, y=0 and M+ is a univalent metal cation. Most preferably, $R_f''$ is fluorine or trifluoromethyl, x=2, y=0 or 1 and M+ is Li+. When x>1, the $R_f''$ groups need not be the same.

The monomer of the present invention is formed by the 2+2 cycloaddition of an unconjugated diene having two terminally unsaturated carbons to a terminally unsaturated substituted fluoroolefin, as taught in general terms by Sharkey, *Fluorine Chemistry Reviews*, 2, P. P. Tarant, Ed., Marcel Dekker, 1968, New York.

Suitable for the practice of the invention are dienes represented by the formula

 (IV)

wherein R is an oxygen, alkylene or alkylene ether group. Preferably, the alkylene group comprises from 2 to about 10 carbon atoms, most preferably 4 to 6 carbon atoms, optionally substituted by one or more ether oxygens, and one or more of the hydrogens may be substituted by halogen. Most preferably, R is an ethenyl or butenyl radical. While it is possible in the practice of the invention to obtain satisfactory results by substituting one or more halogens for one or more hydrogens in R, halogen substitution is not preferred.

Suitable terminally unsaturated fluoroolefins are represented by the formula

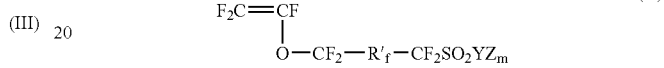 (V)

wherein $R_f'$ is a bond or is a fluoroalkylene or fluoroalkylene ether group, Y is F or O, Z is a univalent metal and m=0 or 1 with the proviso that m=0 when Y is F, and m=1 when Y is O, $R_f$ being ionizable in character when m=1.

In a preferred embodiment, the terminally unsaturated fluoroolefin is represented by the formula

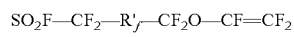

wherein $R_f'$ is a bond or is a fluoroalkylene group of from 1 to about 10 carbon atoms, optionally substituted by one or more ether oxygens and one or more hydrogen atoms; more preferably the terminally unsaturated fluoroolefin is represented by the formula

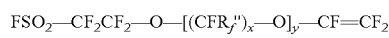

where $R_f''$ is perfluoroalkenyl or fluorine, x=0, 1, 2, 3, or 4, y=0, 1, 2, or 3 with the proviso that when x=0, y=0. Most preferably, $R_f''$ is fluorine or trifluoromethyl, x=2, y=0 or 1.

The dienes suitable for the practice of the invention are well-known in the art and many are widely available commercially.

The terminally unsaturated fluoroolefins suitable for the practice of the invention, as represented by (V), encompass a wide range of compositions. Various of these compositions are described in U.S. Pat. Nos. 3,282,875, 4,358,545, and 5,463,005.

In one embodiment of the 2+2 cycloaddition process of the invention, the diene and terminally unsaturated olefin are combined in a sealed, preferably corrosion resistant, pressure vessel, the olefin being present at a level of less than 50 mol-%, preferably less than 20 mol-%, heated under pressure to a temperature in the range of 180–250° C., preferably 190–210° C., and held for 4–12 hours, preferably 5–7 hours, followed by cooling. Preferably, the reaction mixture is subject to agitation. Suitable pressures range from autogenous pressure to as much as 2,000 atmospheres.

In a second embodiment of the 2+2 cycloaddition process of the invention, the diene and terminally unsaturated olefin may be reacted according the method of Sharkey, op. cit., wherein the reactants are fed continuously as gases to a tube heated to temperatures as high as 600° C. and therein being reacted, the reaction product being continuously removed.

It is a particularly surprising aspect of the present invention that under the preferred conditions of reaction, the 2+2 cycloadduct is made to high yield and purity, with little or no sign of either cyclodimerization of the olefin nor thermal degradation of the fluoroethersulfonyl- containing pendant group. The art teaches the formation of the cycloadduct of TFE with unconjugated dienes, and the cycloadduct of perfluoro(3,6-dioxa-4-methyl-7-octenesulfonyl fluoride) with conjugated dienes. It is known in the art that longer chain fluorinated alkenes are less reactive than TFE, and in particular, perfluoro(3,6-dioxa-4-methyl-7-octene-sulfonyl fluoride) is considerably less reactive than TFE. On the other hand, it is known that unconjugated dienes are less reactive than conjugated dienes.

Glazkov, op. cit., teaches the formation of the 2+2 cycloadduct of perfluoro(3,6-dioxa-4-methyl-7-octenesulfonyl fluoride) and conjugated dienes at temperatures of ca. 140° C. or possibly somewhat higher temperature. However, as hereinbelow demonstrated, no reaction is observed when an unconjugated diene is substituted for the conjugated diene of Glazkov.

One of skill in the art would know to increase the reaction temperature to achieve higher reactivity. But, in this case, Kartsov et al, Zhur. Organ. Khimii, 26 pp. 1573ff (1992), teach that perfluoropropyl vinyl ether, of which perfluoro-(3,6-dioxa-4-methyl-7-octenesulfonyl fluoride) is a derivative, undergoes isomerization and oligomerization in the temperature range from 160–205° C. Thus at temperature much above Glazkov's, and particularly in the range of 200° C., one of skill in the art might well be discouraged from attempting the 2+2 cycloaddition of perfluorosulfonyl vinyl ether-containing species and an unconjugated diene.

The successful achievement of the desired cycloaddition at temperatures in the vicinity of 200° C. is thus quite a surprising and beneficial result.

The 2+2 cycloadduct so formed is represented by the formula (III), as hereinabove described.

In the process of the invention, the monomer of the invention (III) is copolymerized with an olfenic comonomer, preferably ethylene, in the presence of a coordination catalyst. Suitable coordination catalysts include the Ziegler-Natta catalysts, preferably a Mg/Ti supported catalyst, metallocene catalysts, and diimine transition metal complexes as disclosed in Brookhart et al, op. ci.t., preferably alpha-diimine nickel and palladium catalysts Any of the methods of polymerization taught in the art hereinabove cited as suitable for olefins are suitable for the practice of the present invention. The presence of a metallocene complex is preferred.

In the preferred polymerization, the temperature at which the process is carried out is about −100° C. to about +200° C., preferably about 0° C. to about 150° C. Ethylene pressure ranges from atmospheric to about 275 MPa. Glassware and metal autoclaves have been found suitable for the practice of the invention. Further details relevant to the preferred polymerization process of the present invention may be obtained by extension from the teachings of Welborn et al., op. cit.

One of skill in the art will know that numerous coordination catalysts suitable for use in effecting polymerizations of olefins are available, and that different combinations of catalyst and reactants will be more or less effective at achieving high yields, or various degrees and types of branching in the final product.

While Barrick discloses a free-radical polymerization process suitable for the cycloadduct formed with butadiene and TFE, coordination polymerizaiton of the cycloadduct of butadiene and PSEPVE has not been accomplished, presumably because of the proximity of the electronegative fluorine containing groups to the olefinic double bond. For the same reason, the cycloadduct formed with pentadiene may polymerize with certain catalysts, but it is not considered to represent a practical monomer. However, the cycloadducts formed with hexadiene and larger homologs polymerize readily to good yield with a large number of catalysts.

In the most preferred embodiments of the present invention, the monomer of the invention is copolymerized with an olefin, preferably ethylene, and subsequently hydrolyzed if necessary, to form an ionic copolymer or an ionomer.

When the polymer formed by the coordination polymerization process of the invention is in the form of a sulfonyl fluoride, the polymer is preferably hydrolyzed by contacting with LiOH, as is known in the art; see for example Doyle (WO 98/20573) to form the lithium sulfate ionomer.

The ionomers of the present invention exhibit room temperature ionic conductivity of ca. $10^{-7}$–$10^{-6}$ S/cm when dry. However, it is found in the practice of the invention that numerous liquids when imbibed into the ionomer of the invention enhance the conductivity by orders of magnitude. Thus it has been found desirable in order to achieve the most useful embodiments of the present invention to form conductive compositions wherein liquids are imbibed into the ionomer of the invention.

The liquid employed will be dictated by the application. In general terms, it has been found in the practice of the invention that conductivity of the liquid-containing ionomer increases with increasing % weight uptake of the liquid, increasing dielectric constant of the liquid, and increasing Lewis basicity of the liquid, while conductivity has been observed to decrease with increasing viscosity and increasing molecular size of the liquid employed. The actual conductivity observed with any given combination of ionomer and liquid will depend upon the particular balance of properties. Thus, while in general a high dielectric constant is preferred, a highly basic solvent of low viscosity, small molecular size and low dielectric constant may provide superior conductivity in a given membrane than a larger, more viscous, less basic solvent having a higher dielectric constant. Of course, other considerations come into play as well. For example, excessive solubility of the ionomer in the liquid may be undesirable. Or, the liquid may be electrochemically unstable in the intended use.

One particularly preferred embodiment comprises the lithium ionomer combined with aprotic solvents, preferably organic carbonates, which are useful in lithium batteries.

In a preferred embodiment of the present invention, the comonomer concentration is preferably 1–10 mol-%, most preferably 2–7 mol-%.

While there is no limit to the shape or proportions of an article formed from the ionomers of the invention, thin films or membranes, preferably in combination with organic carbonates, are of particular utility for use as separators in lithium batteries, serving therein as single-ion conducting solid polymer electrolytes.

The ionomers of the invention are not fully thermoplastic and are not as readily processable by thermoplastic methods. It may be convenient to form membranes of the sulfonyl fluoride-containing polymer of the invention by using a screw extruder and a flat die. Alternatively, films can be melt pressed. The film so formed may then be converted to the desired ionic form by contacting it with LiOH to form the lithium sulfonate ionomer.

In an additional alternative, films may be cast from solutions or dispersions of the sulfonyl fluoride polymer or of the ionic polymers of the invention by casting onto a substrate and coagulating. No particular method is preferred over another, and the specific method will be chosen according to the needs of the particular practitioner.

In one particularly preferred embodiment of the invention, the ionomer of the invention is incorporated into an electrode suitable for use in lithium batteries. The preferred electrode of the invention comprises a mixture of one or more electrode active materials in particulate form, the ionomer of the invention, at least one electron conductive additive, and at least one organic carbonate. Examples of useful anode active materials include, but are not limited to, carbon (graphitic, coke-type, mesocarbons, polyacenes, and the like) and lithium-intercalated carbon, lithium metal nitrides such as $Li_{2.6}Co_{0.4}N$, tin oxide-based glasses, lithium metal, and lithium alloys, such as alloys of lithium with aluminum, tin, magnesium, silicon, manganese, iron, and zinc. Lithium intercalation anodes employing carbon are preferred. Useful cathode active materials include, but are not limited to, transition metal oxides and sulfides, lithiated transition metal oxides and sulfides, and organosulfur compounds. Examples of such are cobalt oxides, manganese oxides, molybdenum oxides, vanadium oxides, sulfides of titanium, molybdenum and niobium, lithiated oxides such as spinel lithium manganese oxides $Li_{1+x}Mn_{2-x}O_4$, chromium-doped spinel lithium manganese oxides $Li_xCr_yMn_zO_4$, $LiCoO_2$, $LiNiO_2$, $LiNi_xCo_{1-x}O_2$ where x is 0<x<1, with a preferred range of 0.5<x<0.95, $LiCoVO_4$, and mixtures thereof. $LiNi_xCo_{1-x}O_2$ is preferred. A highly preferred electron conductive aid is carbon black, preferably Super P carbon black, available from the MMM S. A. Carbon, Brussels, Belgium, in the concentration range of 1–10%. Preferably, the volume fraction of the lithium ionomer in the finished electrode is between 4 and 40%.

The electrode of the invention may conveniently be made by dissolution of all polymeric components into a common solvent and mixing together with the carbon black particles and electrode active particles. For cathodes the preferred electrode active material is $LiNi_xCo_{1-x}O_2$ wherein 0<x<1, while for anodes the preferred electrode active material is graphitized mesocarbon microbeads. For example, a preferred lithium battery electrode of the invention can be fabricated by dissolving ionomer of the invention in a mixture of acetone and dimethyl-formamide, followed by addition of particles of electrode active material and carbon black, followed by deposition of a film on a substrate and drying. The resultant preferred electrode will comprise electrode active material, conductive carbon black, and ionomer of the invention, where, preferably, the weight ratio of ionomer to electrode active material is between 0.05 and 0.8 and the weight ratio of carbon black to electrode active material is between 0.01 and 0.2. Most preferably the weight ratio of ionomer to electrode active material is between 0.1 and 0.25 and the weight ratio of carbon black to electrode active material is between 0.02 and 0.1. This electrode can then be cast from solution onto a suitable support, such as a glass plate or current collector metal foil, and formed into a film using techniques well-known in the art. The electrode film thus produced can then be incorporated into a multilayer electrochemical cell structure by lamination, as hereinbelow described.

It may be desirable to incorporate into the electrode composition of the invention such adjuvants as may be useful for such purposes as improving the binding of the components thereof, or providing improved structural integrity of an article fabricated therefrom. One particularly preferred additional material is $SiO_2$ which may be incorporated simply by dispersing the particles thereof into the same solution from which the electrode is being formed, as hereinabove described. Preferred are silica particles of an average particle dimension of less than 1.0 micrometers, the silica being present in the admixture at up to 50% by weight of the total.

In an alternative process, the dispersion of electrode-active material and optional carbon black and other adjuvants can first be cast onto a surface followed by addition of the ionomer of the invention in organic carbonate solution.

The invention is further described in the following specific embodiments.

EXAMPLES

Comparative Example 1

12.5 g 1,5-hexadiene and 2.0 g of PSEPVE ($CF_2$=$CFOCF_2CF(CF_3)OCF_2CF_2SO_2F$) prepared in the manner described in D. J. Connally and W. F. Gresham, U.S. Pat. No. 3,282,875 (1966), were combined in a sealed, heavy-walled glass tube and heated to 80° C. and held for 18 h, then heated to 120° C. and held for 6 h, and then heated to 155° C. and held for 6 h. GC analysis after each heating step showed only starting material was present. No reaction took place.

Example 1

100 g 1,5-hexadiene, 50 g PSEPVE, and 1 g of 2,2,6,6-tetramethyl-1-piperidinyloxy (TEMPO, Aldrich Chemical Co.), were combined in a 400 cc Hastelloy C shaker tube heated to 200° C. and shaken for 6 hours. The contents were cooled and distilled to give recovered 1,5-hexadiene and a residue. The residue was then distilled in a Kugelrohr distillation appartus to afford 34.3 g of liquid, bp 50° C. at 0.0001 torr, (58% yield based on PSEPVE) whose infrared, GC-MS, $^1H$ and $^{19}F$ NMR spectra were consistent with a mixture of cis/trans isomers of the cycloaddition product.

Example 2

A mixture of 100 g 1,7-octadiene and 60 g PSEPVE was heated in a 400 cc Hastelloy C skaker tube at 200° C. for 6 hours. In a second tube, a duplicate mixture of 100 g 1,7-octadiene and 60 g PSEPVE was treated in the same way. The tubes were cooled, the contents from the tubes combined and distilled to give recovered 1,7-octadiene and 94.8 g of liquid, bp 95–100° C. at 0.25 torr, (63% yield based on PSEPVE) whose infrared, GC-MS, $^1H$ and $^{19}F$ NMR spectra were consistent with a mixture of cis/trans isomers of the desired cycloadduct.

Example 3

A Constructive Example 10 g (18 mmol) of the cycloadduct of PSEPVE/1,7-octadiene of Example 2, 100 mL of anhydrous methanol, and 1.5 g lithium carbonate (20 mmol) is combined in a 250 mL flask and stirred under a blanket of nitrogen for 3 days at room temperature. The resulting slurry is filtered, and the filtrate is concentrated under vacuum and dried in a stream of warm (50° C.) nitrogen to afford 9.5 g (94% yield) of white solid, which is identified by its $^1H$ and $^{19}F$ NMR spectrum indicating the formation of the lithium sulfonate salt of the sulfonyl fluoride of Example 2.

Example 4

Figure 1:
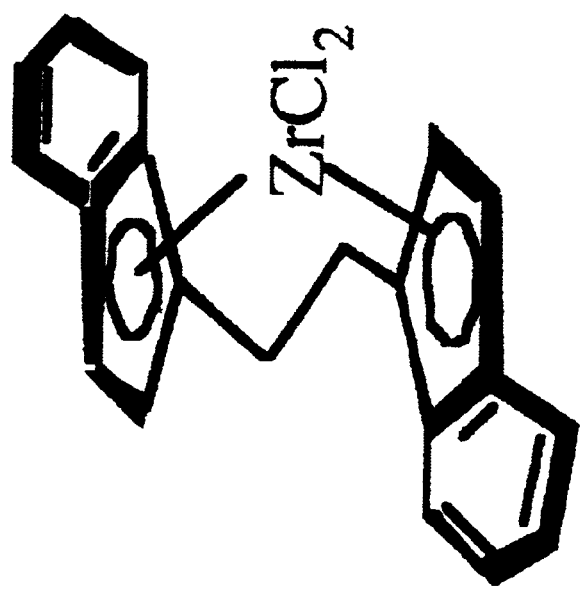
FIG. 1 depicts the metallocene coordination catalyst rac-ethylenebis-(indenyl)zirconium(IV) dichloride.

3.2 mg (0.0077 mmol) of the catalyst rac-ethylenebis (indenyl)zirconium (IV) dichloride, depicted in FIG. 1, and the cycloadduct of PSEPVE/1,7-octadiene of Example 2 (5.0 g, 8.99 mmole) were mixed with 35 mL toluene in a Schlenk flask in a drybox. This was placed under 1 atm of ethylene and was purged with ethylene for 15 min at 0° C. Polymethylalumoxane (PMAO, 5.5 mL 12.9 wt % toluene solution) was added to the mixture. Upon stirring under 1 atm of ethylene at 0° C. for 60 min, 5 mL methanol was slowly added to the reaction mixture. The mixture was then poured into 150 mL methanol, followed by addition of 4 mL conc. HCl. After stirring at RT for 20 min, the white solid polymer was filtered, washed with methanol and dried in vacuo. Copolymer(6.98 g) was obtained. Based on $^{13}$C NMR, the comonomer incorporation was 2.2 mole %. The copolymer exhibits a melting point of 106° C. by differential scanning calorimetry. Gel permeation chromatography (TCB, 135° C., Polyethylene standard): Mw=58,100; Mn=6,150; Mw/Mn=9.5.

Example 5

3.2 mg (0.0077 mmol) of the catalyst rac-ethylenebis (indenyl)zirconium (IV) dichloride, depicted in FIG. 1, and the cycloadduct of PSEPVE/1,7-octadiene of Example 2 (12.0 g, 21.6 mmole) were mixed with 28 mL toluene in a Schlenk flask in a drybox. This was placed under 1 atm of ethylene and was purged with ethylene for 15 min at 0° C. PMAO (5.5 mL 12.9 wt % toluene solution) was added to the mixture. Upon stirring under 1 atm of ethylene at 0° C. for 15 min, 5 mL methanol was slowly added to the reaction mixture. The mixture was then poured into 150 mL methanol, followed by addition of 6 mL conc. HCl. Upon stirring at RT for 20 min, the white solid polymer was filtered, washed with methanol and dried in vacuo. Copolymer(8.93 g) was obtained. Based on $^{13}$CNMR, the comonomer incorporation was 6.0 mole %.

Example 6

12.2 mg (0.017 mmol) of the nickel catalyst depicted in FIG. 2 and the cycloadduct of PSEPVE/1,7-octadiene of Example 2 (8.0 g, 14.4 mmole) were mixed with 35 mL toluene in a Schlenk flask in a drybox. This was placed under 1 atm of ethylene and was purged with ethylene for 15 min at 0° C. PMAO (1.2 mL 12.9 wt % toluene solution) was added to the mixture. Upon stirring under 1 atm of ethylene at 0° C. for 45 min, 5 mL methanol was slowly added to the reaction mixture. The mixture was then poured into 150 mL methanol, followed by addition of 2 mL conc. HCl. Upon stirring at RT for 20 min, the white solid polymer was filtered, washed with methanol and dried in vacuo. Copolymer (0.274 g) was obtained. Based on $^{19}$FNMR and $^1$HNMR, the comonomer was incorporated. The copolymer exhibits a melting point of 98° C. by differential scanning calorimetry. Gel permeation chromatography (TCB, 135° C., Polyethylene standard): Mw=39,900; Mn=1,260; Mw/Mn=32.

Comparative Example 2

3.2 mg (0.0077 mmol) of the catalyst rac-ethylenebis (indenyl)zirconium (IV) dichloride depicted in FIG. 1 and 2,2,3,3-tetrafluorocyclobutyl ethylene (6.5 g) were mixed with 35 mL toluene in a Schlenk flask in a drybox. This was placed under 1 atm of ethylene and was purged with ethylene for 15 min at 0° C. PMAO (5.5 mL 12.9 wt % toluene solution) was added to the mixture. Upon stirring under 1 atm of ethylene at 0° C. for 25 min, 5 mL methanol was slowly added to the reaction mixture. The mixture was then poured into 200 mL methanol, followed by addition of 5 mL conc. HCl. Upon stirring at RT for 20 min, the white solid polymer was filtered, washed with methanol and dried in vacuo. White polymer (2.687 g) was obtained. Based on $^1$HNMR, it is ethylene homopolymer. No comonomer incorporation was observed. $^{19}$FNMR was in agreement with $^1$HNMR. The copolymer exhibits a melting point of 126° C. by differential scanning calorimetry.

Comparative Example 3

12.2 mg (0.017 mmol) of the nickel catalyst depicted in FIG. 2 and 2,2,3,3-tetrafluorocyclobutyl ethylene (6.5 g) were mixed with 35 mL toluene in a Schlenk flask in a drybox. This was placed under 1 atm of ethylene and was purged with ethylene for 15 min at 0° C. PMAO (1.2 mL 12.9 wt % toluene solution) was added to the mixture. Upon stirring under 1 atm of ethylene at 0° C. for ca. 3 hr, 5 mL methanol was slowly added to the reaction mixture. The mixture was then poured into 200 mL methanol, followed by addition of 2 mL conc. HCl. Upon stirring at RT for 20 min, the white solid polymer was filtered, washed with methanol and dried in vacuo. White polymer (1.044 g) was obtained. Based on $^1$HNMR, it is ethylene homopolymer. No comonomer incorporation was observed. $^{19}$FNMR was in agreement with $^1$HNMR. The copolymer exhibits a melting point of 98° C. by differential scanning calorimetry. Gel permeation chromatography (TCB, 135° C., Polyethylene standard): Mw=167,000; Mn=67,500; Mw/Mn=2.5.

Example 7

Melt-pressed films (3.75 cm×3.75 cm to 7.5 cm×7.5 cm) were obtained by placing approximately 0.25–1.0 g of the dried polymer of Example 4 between two sheets of Kapton® Polyimide Film (available from DuPont, Wilmington, Del.) and inserting between the platens of a hydraulic press (model P218C, Pasadena Hydraulic Industries, City of Industry, Calif.) equipped with Omron Electronics Inc. (Schaumburg, Ill.) E5CS temperature controllers. The polymer was preheated for two minutes at 140° C., then pressed at 2500 psi, followed by cooling under pressure.

The film was hydrolyzed and lithiated by treatment with filtered 1.0 M LiOH solution in 1:1 water/methanol. (The flask was heated in an oil bath where the temperature was monitored/controlled by thermocouple and a Yokogawa UT320 Digital Indicating Controller.) The film was placed in a 500 mL flask with 300 mL of the filtered LiOH solution. The reaction was heated to 80° C. for 6 hours, then allowed to cool to room temperature. The LiOH solution was replaced with a 1:1 water/methanol solution and the film was soaked overnight at room temperature. The solution was then replaced with fresh 1:1 water/methanol and heated to 80° C. for 4 hours. The film was dried in a VWR Model 1430 vacuum oven available from VWR Scientific, West Chester, Pa., at a vacuum of ca. 220 Torr and a temperature of 65° C. Further drying of the film under vacuum at elevated temperature (70–100° C.) was performed prior to conductivity testing.

Example 8

The polymer crumb of Example 5 was placed in a 500 mL flask with a stir bar and 350 mL of filtered 1.0 M LiOH in 1:1 water/methanol.

The reaction was heated at 65° C. for 6 hours, then cooled to room temperature. (The flask was heated in an oil bath where the temperature was monitored/controlled by thermocouple and a Yokogawa UT320 Digital Indicating Controller.) The polymer was collected by filtration and placed in a flask with 1:1 water/methanol and soaked at room temperature overnight. The polymer was again collected by filtration, placed in fresh 1:1 water/methanol, and heated to 65° C. for 4 hours with stirring. The rinsed polymer was then collected by filtration. Films were cast by dissolving 0.5 g of the polymer in hot 1:1 cyclohexanone/o-dichlorobenzene and pouring into a 50 mm diameter Teflon® PFA petri dish. The solvent was allowed to evaporate slowly to yield a film. Further drying of the film under vacuum at elevated temperature (70–100° C.) was performed prior to conductivity testing.

Examples 9–14

The hydrolyzed films were dried dried in a recirculating nitrogen oven (Electric Hotpack Company, Inc., Model 633, Philadelphia, Pa.) at 100° C. for 48 hours.

The dried hydrolyzed films were transferred to a sealed container from the vacuum oven while still warm and conveyed to a glove box having a positive pressure of dry nitrogen applied thereto, wherein the membrane was removed from the sealed container and allowed to come to room temperature. Still in the glove box, the membrane was then cut into several sections 1.0 cm by 1.5 cm in size. Typically, the specimens as prepared were then heated at 100° C. under vacuum for 24–48 hours.

A cooled 1.0 cm by 1.5 cm membrane sample was then soaked in an excess of one or more liquids in a sealed glass vial for 24 hours at room temperature. The liquids employed are all commercially available, and were used as received. Following immersion, the membrane sample was removed from the liquid bath, blotted with a paper towel to remove excess liquid, and tested.

Ionic conductivity was determined using the so-called four-point probe technique described in an article entitled "Proton Conductivity of Nafion® 117 As Measured by a Four-Electrode AC Impendance Method" by Y. Sone et al., J. Electrochem. Soc., 143,1254 (1996). The method as described applies to aqueous electrolyte membranes. The method was modified for purposes of obtaining the measurements reported herein for non-aqueous solvents by placing the apparatus described in a sealed glove box purged with dry nitrogen in order to minimize any exposure to water. The method was also modified by, substituting parallel linear probes traversing the full width of the test specimen for the point probes employed in the published method.

A 1.0 cm by 1.5 cm film was blotted dry and positioned into the conductivity cell. Cell impedance was determined over the range of 10 Hz to 100,000 Hz, and the value with zero phase angle in the higher frequency range (usually 500–5000 Hz) was ascribed to the bulk sample resistance in Ohms. The raw resistance value was then converted to conductivity, in S/cm, using the cell constant and liquid-swollen film thickness.

Example 9

A cooled 1.0 cm by 1.5 cm membrane sample of the hydrolyzed film of Example 7 dried in the manner hereinabove described was soaked in an excess of dimethylsulfoxide (ACS grade, 99.9+%, Alfa Aesar, Ward Hill, Mass.) in a sealed glass vial for 24 hours at room temperature. The membrane was removed from the DMSO bath blotted with a paper towel to remove excess solvent, and tested using the four point probe test described above. Conductivity was greater than $10^{-4}$ S/cm.

Example 10

A further 1.0 cm by 1.5 cm membrane sample prepared in the manner of Example 9, was treated according to the method therein described except that the solvent was a 1:1 by volume mixture of propylene carbonate (99%, Aldrich Chemical Co., Inc., Milwaukee, Wis.) and dimethoxyethane (98%, Aldrich Chemical Co., Inc., Milwaukee, Wis.). The conductivity was greater than $10^{-5}$ S/cm.

Example 11

A 1.0 cm by 1.5 cm membrane sample prepared in the manner of Example 9 was treated according to the method therein described except that the solvent was gamma-butyrolactone (99%, Aldrich Chemical Co., Inc., Milwaukee, Wis.). The conductivity was greater than $10^{-5}$ S/cm.

Example 12

A 1.0 cm by 1.5 cm membrane sample prepared in the manner of Example 9 was treated according to the method therein described except that the membrane sample was removed from the dry box environment and heated to 80° C. in deionized water on a hot plate (PMC 730 Series, Dataplate Digital Hot Plate). After allowing the membrane and water bath to cool, the membrane sample was removed, blotted with a paper towel, and tested using the four point probe test described above. The conductivity was greater than $10^{-4}$ S/cm.

Example 13

A 1.0 cm by 1.5 cm membrane sample prepared in the manner of Example 12 was treated according to the method therein described except that following the heating in a deionized water bath, the membrane was immersed into an excess of 1.0 M nitric acid (Reagent grade, EM Science, Gibbstown, N.J.) and heated to T=80° C. for one hour. Following this procedure, the membrane was rinsed with deionized water for several hours. The membrane was clear and intact after this procedure. Following this, the membrane was characterized according to the procedures given above and the conductivity was greater than $10^{-3}$ S/cm.

Example 14

A cooled 1.0 cm by 1.5 cm membrane sample of the hydrolyzed film of Example 8 dried in the manner hereinabove described was then soaked in an excess of a 1:1 by volume mixture of ethylene carbonate (98%, Aldrich Chemical Co., Inc., Milwaukee, Wis.) and dimethyl carbonate (99%, Alfa Aesar, Ward Hill, Mass.) in a sealed glass vial for 2 hours at room temperature. The membrane was removed from the solvent bath, blotted with a paper towel to remove excess solvent, and tested using the four point probe test described above. Solvent uptake was 319%. Conductivity was greater than $10^{-4}$ S/cm.

What is claimed is:

1. A terminally unsaturated olefin of the formula

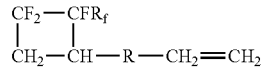 (III)

wherein R is oxygen or an alkylene or alkylene ether group wherein one or more of the hydrogens may be substituted by halogen, and $R_f$ is a radical of the formula

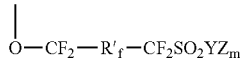 (II)

wherein $R'_f$ is a bond or is a fluoroalkylene or fluoroalkylene ether group, Y is F or O, Z is a univalent metal and m=0 or 1 with the proviso that m=0 when Y is F, and m=1 when Y is O, $R_f$ being ionizable in character when m=1.

2. The terminally unsaturated olefin of claim 1 wherein Rf is the radical represented by the formula $$FSO_2—CF_2CF_2—O—[(CFR_f'')_x—O]_y—$$

wherein $R_f''$ is perfluoroalkyl or fluorine, x=0,1,2,3, or 4, y=0,1,2, or 3, with the proviso that when x=0, y=0.

3. The terminally unsaturated olefin of claim 2 wherein $R_f''$ is fluorine or trifluoromethyl, x=2, y=0 or 1.

4. The terminally unsaturated olefin of claim 1 wherein $R_f$ is the radical represented by the formula $$M^+SO_3^-—CF_2CF_2—O—[(CFR_f'')_x—O]_y—$$

where $R_f''$ is perfluoroalkyl or fluorine, x=0,1,2,3, or 4, y=0,1,2, or 3, with the proviso that when x=0, y=0, and $M^+$ is a univalent metal cation.

5. The terminally unsaturated olefin of claim 4 wherein $R_f''$ is fluorine or trifluoromethyl, x=2, y=0 or 1 and $M^{+\ is\ Li+}$.

6. A process for producing terminally unsaturated olefin of claim 3, the process comprising combining in a vessel a diene of the formula

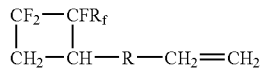 (III)

wherein R is oxygen or an alkylene or alkylene ether group wherein one or more of the hydrogens may be substituted by halogen, with up to 50 mol-% of a terminally unsaturated fluoroolefin having the formula

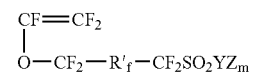 (V)

wherein $R'_f$ is a bond or is a fluoroalkylene or fluoroalkylene ether group, Y is F or O, Z is a univalent metal and m=0 or 1 with the proviso that m=0 when Y is F, and m=1 when Y is O, $R_f$ being ionizable when m=1;

heating to a temperature in the range of 180–600° C. for a period of about one second to about 24 hours.

7. The process of claim 6 wherein R in the diene is ethenyl or butenyl, and the terminally unsaturated olefin is represented by the formula $$FSO_2—CF_2CF_2—O—[(CFR_f'')_x—O]_y—CF=CF_2$$

where $R_f''$ is perfluoroalkenyl or fluorine, x=0,1,2,3, or 4, y=0,1,2, or 3 with the proviso that when x=0, y=0.

8. The process of claim 6 wherein $R_f''$ is fluorine or trifluoromethyl, x=2, y=0 or 1.

9. The process of claim 6 followed by cooling and removal of product.

10. The process of claim 6 further including simultaneous passage of diene and F-olefin through a heated tube.

* * * * *